(12) United States Patent
Janssen

(10) Patent No.: US 10,519,049 B2
(45) Date of Patent: *Dec. 31, 2019

(54) ANTI-MICROBIAL ADDITIVE FOR USE IN FLOWER VASE WATER

(71) Applicant: Enhold B.V., Naarden (NL)

(72) Inventor: Johannes Antonius Marie Janssen, Almere (NL)

(73) Assignee: Enhold B.V., Naarden (NL)

( * ) Notice: Subject to any disclaimer, the term of this patent is extended or adjusted under 35 U.S.C. 154(b) by 0 days.

This patent is subject to a terminal disclaimer.

(21) Appl. No.: 15/897,859

(22) Filed: Feb. 15, 2018

(65) Prior Publication Data

US 2018/0170776 A1  Jun. 21, 2018

Related U.S. Application Data

(63) Continuation of application No. 12/989,952, filed as application No. PCT/NL2008/050258 on Apr. 28, 2008, now Pat. No. 9,963,364.

(51) Int. Cl.
*C02F 1/50* (2006.01)
*A01N 3/02* (2006.01)

(52) U.S. Cl.
CPC . *C02F 1/50* (2013.01); *A01N 3/02* (2013.01)

(58) Field of Classification Search
CPC .................................. C02F 1/50; A01N 3/02
See application file for complete search history.

(56) References Cited

U.S. PATENT DOCUMENTS

| | | | |
|---|---|---|---|
| 5,284,818 A | 2/1994 | Shafer et al. | |
| 5,298,478 A | 3/1994 | Yamamoto et al. | |
| 5,607,681 A | 3/1997 | Galley et al. | |
| 6,261,829 B1 | 7/2001 | Lehtonen | |
| 6,303,326 B1 | 10/2001 | Felton et al. | |
| 9,963,364 B2 * | 5/2018 | Janssen | A01N 3/02 |

| | | | |
|---|---|---|---|
| 2005/0175748 A1 | 8/2005 | Thijssen et al. | |
| 2005/0221029 A1 | 10/2005 | Cater et al. | |
| 2007/0240728 A1 | 10/2007 | Hashimoto et al. | |
| 2008/0125320 A1 | 5/2008 | Coats | |

FOREIGN PATENT DOCUMENTS

| | | |
|---|---|---|
| EP | 1 289 854 B1 | 8/2004 |
| WO | WO-01/50853 | 7/2001 |
| WO | WO-02/08377 A1 | 1/2002 |
| WO | WO-2006/035320 A2 | 4/2006 |
| WO | WO-2006/138271 A1 | 12/2006 |

OTHER PUBLICATIONS

Doi, Motoaki et al., "Sucrose Improves the Postharvest Life of Cut Flowers of a Hybrid Limonium," Hort Science, vol. 30, No. 5, Aug. 1, 1995, pp. 1058-1060.

International Search Report dated Jan. 7, 2009 in corresponding Application No. PCT/NL2008/050258, 5 pgs.

Tiina et al., "Antibacterial effect of the glucose oxidase-glucose system on food-poisoning organisms", International Journal of Food Microbiology, 1989, vol. 8, pp. 165-174.

* cited by examiner

*Primary Examiner* — Mina Haghighatian
(74) *Attorney, Agent, or Firm* — Gilberto M. Villacorta; Sunit Talapatra; Foley & Lardner LLP

(57) ABSTRACT

The present invention relates to anti-microbial compositions that may advantageously be added to vase water of cut flowers in order to prevent microbial growth, especially in vase water containing added cut flower nutrients and/or water uptake stimulants.

One aspect of the invention relates to the use of an EC 1.1.3 oxidoreductase as an antimicrobial additive for vase water of cut flowers.

Another aspect of the invention concerns a method of putting cut flowers into vase water, said method comprising immersing the stems of one or more cut flowers into vase water and adding an antimicrobial composition containing an EC 1.1.3 oxidoreductase to the vase water before, after or at the same time as the cut flowers are immersed into the vase water

16 Claims, No Drawings

ANTI-MICROBIAL ADDITIVE FOR USE IN FLOWER VASE WATER

CROSS-REFERENCE TO RELATED APPLICATIONS

This application is a Continuation of U.S. patent application Ser. No. 12/989,952, filed Oct. 27, 2010, which is the U.S. National Phase of International Patent Application No. PCT/NL2008/050258, published on Nov. 5, 2009 as WO 2009/134118 A1. The contents of these applications are herein incorporated by reference in their entirety.

TECHNICAL FIELD OF THE INVENTION

The present invention relates to anti-microbial compositions that may advantageously be added to vase water of cut flowers in order to prevent microbial growth, especially in vase water containing added cut flower nutrients and/or water uptake stimulants.

BACKGROUND OF THE INVENTION

It is known that the vase life of cut flowers can be extended by use of nutrients and/or water uptake stimulants in combination with certain chemical preservatives. Examples of such nutrients include carbohydrates such as sucrose, fructose, glucose, lactose and maltose. Examples of water uptake stimulants include acidulants, such as citric acid, glycolic acid, malic acid and aluminium sulphate, and anionic and non-ionic surfactants. Chemical preservatives currently in use include biocides, such as isothiazolinones, bronopol and quaternary ammonium salts. Several flower conditioning compositions which contain various mixtures are commercially available, e.g., Chrysal®. These compositions are effective in extending the vase life of cut flowers up to several days. Doi and Reid, *Hort. Science* 30: 1058-1060 (1995), describe a vase solution containing Physan (a benzalkonium disinfectant) and sucrose, which prolonged the florets life but also promoted bud opening.

Biocides have been employed to inhibit growth of microorganisms such as bacteria and algae. Microbial growth has an unfavourable effect on the effectiveness of cut flower nutrients and water uptake stimulants that have been dissolved in vase water, thus adversely affecting the longevity of the flowers, while in addition turning the water murky and causing it to smell foul.

SUMMARY OF THE INVENTION

The present inventors have unexpectedly discovered that growth of micro-organisms in vase water of cut flowers can be inhibited very effectively by adding an EC 1.1.3. oxidoreductase to the vase water. The anti-microbial effect of the oxidoreductase is particularly pronounced in case the vase water contains nutrients that favour the growth of micro-organisms. The addition of the EC 1.1.3. oxidoreductase to vase water advantageously occurs at about the same time that fresh cut flowers are immersed therein. Thus, it is ensured that the vase water will remain clear for a prolonged period of time. In addition, introduction of the oxidoreductase prevents the development of foul smells and helps to extend the vase life of cut flowers.

Oxidoreductases to be used in the antimicrobial additive of the invention are selected from oxidoreductases of Enzyme Classification (EC) 1.1.3, i.e. oxidases which use hydroxymethylene groups (>CH—OH) as hydrogen donors (electron donors) and molecular oxygen as a hydrogen acceptor. Examples thereof are glucose oxidases (EC 1.1.3.3), hexose oxidases (EC 1.1.3.4), galactose oxidases (EC 1.1.3.9) and alcohol dehydrogenase (EC 1.1.3.13). These oxidases are capable of catalysing the oxidation of a particular substrate (e.g. glucose to δ-gluconolactone in the case of glucose oxidase, ethanol to acetaldehyde in the case of alcohol dehydrogenase) and the concurrent reduction of oxygen to hydrogen peroxide.

Without wishing to be bound by theory, the inventors believe that the antibacterial mode of action is probably due to both the oxidative potential of hydrogen peroxide and the presence of the oxidation products, such as δ-gluconolactone which is a known glycosyltransferase inhibitor. In addition, the oxidation of substrate (e.g. hexose or ethanol) will reduce oxygen levels in the vase water, thereby inhibiting the growth of aerobic micro-organisms.

DETAILED DESCRIPTION OF THE INVENTION

Accordingly, one aspect of the invention relates to the use of an EC 1.1.3 oxidoreductase as an antimicrobial additive for vase water of cut flowers.

In accordance with a particularly preferred embodiment of the present invention, the EC 1.1.3 oxidoreductase is selected from the group consisting of glucose oxidases (EC 1.1.3.3), hexose oxidases (EC 1.1.3.4), galactose oxidases (EC 1.1.3.9), alcohol dehydrogenase (EC 1.1.3.13) and combinations thereof. Each of these oxidases can be employed effectively to prevent microbial growth in the vase water, efficacy depending on the enzyme substrate levels in the vase water.

Most preferably, the EC 1.1.3 oxidoreductase employed in the antimicrobial additive is glucose oxidase. The unit of oxidase is usually expressed as the activity in terms of conversion of the substrate. For glucose oxidase, a suitable unit is the SRU (Sarett Unit), wherein 1 SRU is equivalent to the conversion of 0.43 mol of glucose to gluconic acid or its lactone per minute a 30° C. in a phosphate buffer at pH 5.1.

Glucose oxidase is preferably added to the vase water in an amount of 1 Sarett Units (SRU) per litre, even more preferably of 5 SRU per litre and most preferably of 10 SRU per litre. Typically, the amount of glucose oxidase activity that is added to the vase water does not exceed 200 SRU per litre. More preferably, the amount of glucose oxidase does not exceed 100 SRU per litre.

The EC 1.1.3 oxidases may be of any origin, preferably microbial. Suitable glucose oxidases may be obtained from fungal origin, e.g. from *Aspergillus niger*.

The antimicrobial effect of the present oxidoreductase will become manifest when the vase water contains substrate that can be converted by the oxidoreductase. Since, these substrates usually are nutrients for most micro-organisms, the anti-microbial action of the oxidoreductase will become apparent when it is needed, i.e. when the conditions are such that microbial growth is favoured.

As mentioned herein before, the present antimicrobial additive is particular effective if it is used to prevent microbial growth in vase water that also contains cut flower nutrients and/or water uptake stimulants. These components usually stimulate microbial growth as micro-organisms can metabolise them. At the same time, these same components may be used as a substrate by the oxidoreductase, which will thus exert its anti-microbial action.

In accordance with a particularly preferred embodiment, the present antimicrobial additive, besides the EC 1.1.3 oxidoreductase, contains one ore more cut flower nutrients and/or one or more water uptake stimulants. Examples of cut flower nutrients that can suitably be employed include sucrose, fructose, glucose, lactose, maltose and combinations thereof. Examples of water uptake stimulants that can advantageously be incorporated in the antimicrobial additive include citric acid, glycolic acid, malic acid, aluminium sulphate, anionic surfactants, non-ionic surfactants and combinations thereof.

The present antimicrobial additive preferably also contains a biocide selected from the group consisting of fungicides, antibiotics, bactericides, yeast inhibitors and combinations thereof. The use of a biocide besides the E.C. 1.1.3 oxidoreductase was found to significantly enhance the antimicrobial effect of the oxidoreductase.

Another aspect of the invention relates to a method of putting cut flowers into vase water, said method comprising immersing the stems of one or more cut flowers into vase water and adding an antimicrobial composition containing an EC 1.1.3 oxidoreductase to the vase water before, after or at the same time as the cut flowers are immersed into the vase water.

The antimicrobial composition employed in accordance with the present invention preferably is largely water-soluble. More particularly, it is preferred that at least 80 wt. %, more preferably 90 wt. % of the antimicrobial composition will dissolve in distilled water of 20° C. when added thereto in an amount of 5 g/l.

The antimicrobial composition advantageously is added to the vase water in the form of a tablet, a powder, a paste or of a fluid having a dry matter content of 5 g/l. Most preferably, said composition is added in the form of a tablet or a powder.

Preferably, the antimicrobial composition employed in accordance with the invention contains glucose oxidase in an amount of 0.1-200 SRU per gram of dry matter, most preferably of 0.5-100 SRU per gram of dry matter.

According to a particularly preferred embodiment, the antimicrobial composition contains 5% by weight of dry matter of a carbohydrate selected from the group consisting of glucose, fructose, sucrose, lactose, maltose and combinations thereof. Even more preferably, the carbohydrate is selected from glucose, sucrose or combinations thereof. Most preferably, the carbohydrate is glucose.

In accordance with another embodiment of the invention, the antimicrobial composition contains one or more acidulants. The incorporation of acidulants in the antimicrobial composition was found to enhance the antimicrobial action of the oxidoreductase. Typical examples of acidulants that may suitably be employed include gluconic acid, glucono-deltalactone, citric acid, tartaric acid, propionic acid, glycolic acid, fumaric acid, sorbic acid, malic acid, aluminium sulphate and combinations thereof. According to a particularly preferred embodiment, the acidulant employed in the present method is selected from the group consisting of gluconic acid, glucono-deltalactone and combinations thereof. Most preferably, the antimicrobial composition contains glucono-deltalactone. Unlike gluconic acid, glucono-deltalactone is solid at ambient temperatures, which makes it easy to incorporate this acidulant into solid formulations such as powders and tablets. When added to vase water, glucono-deltalactone will gradually convert to gluconic acid, thereby causing a pH decrease of the vase water.

Advantageously, the pH of the vase water is reduced by 1.0 pH units, more preferably by 1.5 pH units and most preferably by 2.0-4.0 pH units as a result of the addition of the present antimicrobial composition.

The present method advantageously employs an antimicrobial composition containing a biocide selected from the group consisting of fungicides, antibiotics, bactericides, yeast inhibitors and combinations thereof. Even more preferably, said biocide is selected from the group consisting of quaternary ammonium compounds containing at least one $C_6$-$C_{24}$ hydrocarbon residue, guanidine compounds containing at least one $C_6$-$C_{24}$ hydrocarbon residue, bromo-nitrogen derivates, isothiazolinones, hydroxyquinolines, 1,3-dihalo-5,5-dimethylhydantoins, chloramphenicol, spectinomycin, alkyl parabens, salicylic acids and salts thereof, benzoic acids and salts thereof, sorbates, thiabendazole1,3-dichloro-5,5-dimethylhydantoin, N-chlorosulfonamides, isocyanurates, lysozymes and combinations thereof. Most preferably, the biocide is selected from the group consisting of quaternary ammonium compounds containing at least one $C_6$-$C_{24}$ hydrocarbon residue, guanidine compounds containing at least one $C_6$-$C_{24}$ hydrocarbon residue and combinations thereof. The biocides belonging to the latter group effectively enhance the antimicrobial action of the oxidoreductase in the vase water.

Typically, the biocide containing antimicrobial composition is added to the vase water to deliver the biocide in a concentration of 0.5-1000 mg/l. Most preferably, in the present method the biocide is added to the vase water in a concentration of 1-200 mg/l.

In order to realise the benefits of the present invention, the antimicrobial composition is typically added to the vase water in an amount of 0.1-40 g/l. More preferably, the antimicrobial composition is added in an amount of 0.5-20 g/l, most preferably of 1-15 g/l.

Yet another aspect of the invention relates to a vessel holding an amount of water and one or more flowers whose stems are at least partially immersed in said water, wherein the water contains glucose oxidase in a concentration of 1-200 SRU per litre. Preferably, the glucose oxidase is contained in the water in a concentration of 5-100 SRU per litre, most preferably in a concentration of 10-50 SRU per litre.

According to another preferred embodiment the vase contains a biocide selected from the group consisting of fungicides, antibiotics, bactericides, yeast inhibitors and combinations thereof. The biocide is advantageously selected from the group consisting of quaternary ammonium compounds containing at least one $C_6$-$C_{24}$ hydrocarbon residue, guanidine compounds containing at least one $C_6$-$C_{24}$ hydrocarbon residue, bromo-nitrogen derivates, isothiazolinones, hydroxyquinolines, 1,3-dihalo-5,5-dimethylhydantoins, chloramphenicol, spectinomycin, alkyl parabens, salicylic acids and salts thereof, benzoic acids and salts thereof, sorbates, thiabendazole1,3-dichloro-5,5-dimethylhydantoin, N-chlorosulfonamides, isocyanurates, lysozymes and combinations thereof.

Biocide is preferably contained in the vase water in a concentration of 0.5-1000 mg/l, more preferably of 0.8-500 mg/l, most preferably of 1-200 mg/l.

The vase water advantageously has a pH of less than 5.5, more preferably a pH of 3.0-5.0 and most preferably of 3.5-4.8.

The various components of the anti-microbial composition of the invention will be described in more detail below. The amounts relate to a single dosage unit of the antimicrobial composition, which typically designed for use in 1 litre of preservative solution (vase water). Typically, a dosage unit of the present anti-microbial composition contains 0.1-40 g of dry matter, more preferably 0.5-20 g of dry matter, most preferably 10 g of dry matter.

If the dosage unit is a measured amount of liquid, the amounts given per unit dosage can be converted to weight per litre in a similar way, depending on the amount of liquid of the dosage unit.

The present anti-microbial composition preferably contains 1-200 SRU, preferably 5-100 SRU, most preferably 10 to 50 SRU of glucose oxidase per dosage unit.

The antimicrobial effect of the oxidoreductase in the present antimicrobial composition is dependent on the presence of the corresponding substrate in the vase water. Such substrate may already be present to some extent in the vase or it may be provided through the present anti-microbial composition or it may be added separately. The total amount of enzyme substrate (alcohol or carbohydrate, e.g. glucose) can be between 100 mg en 50 g per litre of vase water solution. Preferably, the amount of enzyme substrate is in the range of 0.2-20 g/l. The enzyme substrate preferably is a carbohydrate selected from the group consisting of glucose, fructose, galactose, sucrose, lactose, maltose and combinations thereof, glucose being most preferred.

In an advantageous embodiment, the present antimicrobial composition contains at least 100 mg, more preferably 0.2-50 g and most preferably 0.2-20 g of carbohydrate per dosage unit, said carbohydrate being selected from the group consisting of glucose, fructose, galactose, sucrose, lactose and combinations thereof. In a 10 g dosage unit of a solid anti-microbial composition substrate, such as glucose, may be incorporated in an amount of up to 9.99 g of dry matter. Preferably, 0 g to 9.8 g of substrate is incorporated in a dry composition of 10 g.

The quaternary ammonium compounds to be used according to the invention are ammonium compounds having four organic groups covalently attached to a nitrogen atom, at least one of which has 6 carbon atoms. They may generally be represented by the formula $R^1R^2R^3R^4N^+X^-$, wherein:

$R^1$ is a $C_6$-$C_{24}$ hydrocarbon group, which may be hetero-substituted, e.g. with one or more halogen atoms;

$R^2$ is a $C_1$-$C_{24}$ hydrocarbon group, which may be hetero-substituted, e.g. with one or more halogen atoms;

$R^3$ and $R^4$ are $C_1$-$C_6$ alkyl groups;

alternatively, $R^1$ and $R^2$, or $R^3$ and $R^4$ may, together with the nitrogen atom, form a saturated or partly unsaturated ring or $R^1$, $R^2$, $R^3$ or $R^4$ may be connected to a second nitrogen atom in the form of a $C_2$-$C_6$ alkylene, cycloalkylene of piperazine group, thus forming dimeric or polymeric quaternary ammonium compounds;

X is halogen or the residue of an organic or inorganic acid.

Examples of quaternary ammonium salts are benzalkonium chloride ($C_{12}$-$C_{18}$ alkyl dimethyl benzyl ammonium chloride), $C_{12}$-$C_{18}$ alkyl dimethyl ethylbenzyl ammonium chloride and didecyl dimethyl ammonium chloride. Combinations may also be used.

Preferably, the quaternary ammonium compound is present in the antimicrobial composition of the invention at a level of 2-500 mg per dosage unit, preferably 5-250 mg per dosage unit, most preferably 10-100 mg per dosage unit.

The guanidine compounds to be used according to the invention are organic compounds containing the guanidine group (—$NR^a$—C(=$NR^b$)—$NR^c$—), wherein $R^a$, $R^b$ and $R^c$ are hydrogen, or a $C_1$-$C_{24}$ hydrocarbon group, optionally substituted e.g. with halogen. At least one group on the nitrogen atoms should preferably contain 6 carbon atoms. Examples of guanidine compounds include chlorhexidine (A—$NCH_3$—C(=NH)—NH—C(=NH)—NH—$(CH_2)_6$—NH—C(=NH)—NH—C(=NH)—$NCH_3$—A, wherein A is p-chlorophenyl, and especially poly-hexamethylene-biguanide (PHMB: [—$(CH_2)_6$—NH—C(=NH)—NH—C(=NH)—NH—]$_n$).

Preferably, the guanidine (biguanide) compound is present in the antimicrobial composition of the invention at a level of 1-100 mg per dosage unit, more preferably 2-60 mg and most preferably 2.5-20 mg guanidine compound per dosage unit.

In a preferred embodiment, the composition additionally comprises an amount of acidulant that is effective in adjusting a pH in a solution (vase water) produced from the composition between 3 and 5.5, preferably between 3.5 and 5.0. In other words, when a dosage unit of the present composition is added to 1 litre if water at ambient temperatures, the acidulants contained therein advantageously reduce the pH of the vase water to within the aforementioned ranges.

The amount of acidulant need to achieve the desired pH reduction depends on the buffering capacity of the antimicrobial composition of the invention and on the water that is used for constituting the vase solution. A typical range is between 10 and 1000 mg per dosage unit, preferably between 50 and 700 mg per dosage unit.

The present composition may suitably contain an anionic or non-ionic surfactant, e.g. in an amount of 1-500 mg per dosage unit. Suitable non-ionic surfactant materials useful for the purposes of this invention include, but are not limited to, non-ionic surfactants such as hexitol anhydrides (hexitans and hexides) derived from sorbitol partially esterified with common fatty acids (e.g. palmitic, stearic and oleic acids). Other suitable nonionic surfactants include materials derived from the latter surfactants by etherification of the free hydroxyl groups with poly(oxyethylene) groups. Additionally, polyethoxylated octyl- or nonylphenols can also be used. Nonionic surfactants comprising ethoxylated straight chain alcohols, as well as nonionic surfactants comprising block copolymers of propylene oxide and ethylene oxide can also be used. Additionally, non-ionic surfactants which are block polymers of polyoxyalkylene derivatives of ethylenediamine may also be used. Suitable anionic surfactants include alkali metals salts of esters of sulfosuccinic acid such as sodium dioctyl sulfosuccinate.

The anti-microbial composition of the present invention can suitably take the form of a liquid, a paste, a powder, a tablet etc. Typically, the water content of the present composition is less than 90 wt. %, more preferably the water content is less than 50 wt. %. The oxidoreductases are preferably used in antimicrobial compositions having low water activity, as the stability of the enzymes in the presence of water is often limited. Thus, according to a particularly preferred embodiment, the present composition contains even less than 10 wt. % of water, e.g. in case of powders or tablets.

The present composition can advantageously be added to vase water to ensure that the water remains clear for a prolonged period of time. The composition preferably produces a fully transparent solution when dispersed in water of 20° C. in an amount of 0.1 g dry matter per litre of water, in particular between 0.2 and 50 g per litre, especially between 0.5 and 20 g per l. The aforementioned requirement does not necessarily imply that the present composition will fully dissolve when added in the aforementioned amounts. However, any undissolved material should not affect the transparent quality of the vase water, e.g. because it forms a layer of sediment at the bottom of the vase. According to a particularly preferred embodiment, the present composition is highly soluble in water.

According to one embodiment of the invention the present composition is a powder or a tablet. When in the form of dry powders, the formulations of this invention are suitably packaged in bulk for end use, as in containers having a tightly-fitting lid such as screw-capped or snap-capped bottles or, preferably are packaged in plastic, foil or paper sachets (see EP-A 1 289 854) containing the required amount of material for a single use. Effervescent ingredients may advantageously be incorporated to accelerate dispersion and dissolving of the composition. Typically, tablets of the present composition have a weight of 0.1-20 g, preferably of 0.5-10 g.

According to another embodiment, the anti-microbial composition of the present invention is a concentrated liquid, preferably comprising 10 g of dry matter per litre up to e.g. 900 g/l, more preferably comprising 25-800 g of dry matter per litre. In case such a liquid contains both oxidoreductase and oxidoreductase substrate, at least one of said components, especially the oxidoreductase, is preferably encapsulated or packed separately to prevent premature oxidation of the substrate.

The present anti-microbial composition is suitably dissolved in vase water at a concentration ranging between about 0.5 g/litre to about 40 g/litre, preferably about 2 g/litre to 20 g/litre, also depending on the weight and the physical nature of the dosage unit. For a typical arrangement of cut flowers, the volume of water in a vase or bucket is about one-half to four litres. Thus, a preferred package comprising a unit dosage of the present composition, is a sachet containing about 0.5-40 grams of the composition, calculated as dry matter, especially 1-40 grams, more particularly 2-20 grams. According to a particularly preferred embodiment, said sachet consists at least partially of water-permeable material such that upon immersion in water, water will readily enter the sachet and come in direct contact with the anti-microbial composition. By immersing such a sachet into vase water, the contents of the sachet will dissolve into the intruding water and diffuse out of the sachet into the vase water. Alternatively, the sachets may consist of water-impermeable material, and may be opened and emptied into the vase upon use.

The present composition, at the levels at which it is to be employed in the vase water, has a pronounced anti-microbial effect, but exhibits essentially no phytotoxic effect.

The invention is further illustrated by means of the following example.

EXAMPLE

A mixed bouquet of 12 flowers composed as follows:
  Rosa 'Passion' (2 stems)
  Chrysanthemum santini 'Noki' (2 stems)
  Chrysanthemum santini 'Quinty' (2 stems)
  Gerbera 'Baya' (2 stems)
  Gerbera 'Sardana' (2 stems)
  Antirrhinum (1 stem)
  Solidago 'Tara' (1 stem)
was placed in a vase with 1 litre of solution. The solution was either tap water or an aqueous base solution containing 10 g/l of a composition containing 94.66% glucose, 5% citric acid, 0.34% conventional biocides.
The following components were added or not to the base solution (quantities per litre solution):
  BZC: 0 or 30 ppm of benzalkonium chloride
  GOX: 0 or 100 SRU of glucose oxidase The results are given in terms of flower life (FL in days), water clearness after x days (WCx, rating from 1—poor to 5—good) and bacterial contamination after 7 days (CFU, in 1000 CFU/g stem: below 10 hardly or not contaminated, 10-100 moderately contaminated, 100-1,000 contaminated, above 1,000 heavily contaminated). The vases with flowers were placed under 12 per 24 hours of 1000 lux, at 20° C.

TABLE

Results of treatments with different preservative solutions

| Base | BZC (ppm) | GOX (SRU) | FL (days) | WC7 | WC10 | CFU (×1000) |
|---|---|---|---|---|---|---|
| −(water) | 0 | 0 | 5.1 | 1.0 | 1.0 | n.d. |
| + | 0 | 0 | 12.5 | 1.5 | 1.0 | 24,600 |
| + | 0 | 100 | 12.7 | 4.0 | 3.0 | 4,400 |
| + | 30 | 0 | 12.0 | 2.5 | 1.5 | 900 |
| + | 30 | 100 | 12.5 | 3.0 | 3.0 | 16 | n.d. = not determined

The results show that the individual components have a clear effect on each parameter. Glucose oxidase has a strong effect on water clearness, whereas glucose oxidase as well as BZC has a strong effect on bacterial contamination. Furthermore, these results demonstrate a synergetic effect resulting from the combined use of glycose oxidase and quarternary ammonium biocide (BZC).

The invention claimed is:

1. A method of extending the life of cut flowers, the method comprising immersing stems of one or more cut flowers into water and, separately, adding a dosage unit of a composition to the water before, after or at the same time as the stems are immersed into the water to provide 0.5-20 g of a dry matter per liter of water, the dosage unit comprising:
   (a) glucose oxidase in an amount of 0.1-200 SRU per gram of dry matter of the composition;
   (b) a carbohydrate selected from the group consisting of glucose, fructose, sucrose, lactose, maltose and combinations thereof.

2. The method according to claim 1, wherein the composition is added to the water in an amount of 0.1-40 g/l.

3. The method according to claim 1, wherein the composition is added to the water in an amount of 0.5 to 20 g/l.

4. The method according to claim 1, wherein the glucose oxidase is added in an amount of 1 to 200 SRU per litre of water.

5. The method according to claim 4, wherein the glucose oxidase is added in an amount of 5 to 100 SRU per litre of water.

6. The method according to claim 1, wherein the glucose oxidase is added in an amount of 10 to 50 SRU per litre of water.

7. The method according to claim 1, wherein the carbohydrate is glucose.

8. The method according to claim 1, wherein at least 90 wt. % of the composition dissolves in distilled water of 20° C. when added thereto in a concentration of 5 g/L.

9. The method according to claim 1, wherein the dosage unit comprises glucose oxidase in an amount of 0.5 to 100 SRU per gram of dry matter of the composition.

10. The method according to claim 1, wherein the dosage unit comprises glucose oxidase in an amount of 1-200 SRU.

11. The method according to claim 1, wherein the addition of the dosage unit to the water causes a pH-reduction of 1.0 to 4.0 pH units.

12. The method according to claim 1, wherein the addition of the dosage unit to the water causes the pH to be reduced to less than pH 5.5.

13. The method according to claim 1, wherein the dosage unit further comprises 50 to 700 mg of an acidulant selected from the group consisting of gluconic acid, glucono-delta-lactone, citric acid, tartaric acid, propionic acid, glycolic acid, fumaric acid, sorbic acid, malic acid, aluminium sulphate and combinations thereof.

14. The method according to claim 1, wherein the dosage unit further comprises a biocide.

15. The method according to claim 14, wherein the biocide is added to the water in a concentration of 0.5-1000 mg/L.

16. The method according to claim 14, wherein the biocide is selected from the group consisting of quaternary ammonium compounds containing at least one hydrocarbon residue, guanidine compounds containing at least one C6-C24 hydrocarbon residue, bromo-nitrogen compounds, isothiazolinones, hydroxyquinolines, 1,3-dihalo-5,5-dimethylhydantoins, chloramphenicol, spectinomycin, alkyl parabens, salicylic acids and salts thereof, benzoic acids and salts thereof, sorbates, thiabendazole, 1,3-dichloro-5,5-dimethylhydantoin, N-chlorosulfonamides, isocyanurates, lysozymes and combinations thereof.

* * * * *